United States Patent [19]

Voges et al.

[11] 4,291,706
[45] Sep. 29, 1981

[54] VALVE FOR CLOSING A PLURALITY OF CONTAINER OUTLETS SIMULTANEOUSLY

[75] Inventors: Karl-Friedrich Voges, Melsungen; Gerd Herlitze, Baunatal, both of Fed. Rep. of Germany

[73] Assignee: Intermedicat GmbH, Emmenbrucke, Switzerland

[21] Appl. No.: 75,131

[22] Filed: Sep. 12, 1979

[30] Foreign Application Priority Data

Sep. 26, 1978 [DE] Fed. Rep. of Germany ... 7828577[U]

[51] Int. Cl.³ .............................................. F16K 11/02
[52] U.S. Cl. ................. 128/762; 137/625.44; 137/625.4; 128/767; 128/275
[58] Field of Search ...................... 137/625.41, 625.44, 137/607, 625.46, 625.4; 251/DIG. 2; 128/762, 275, 295

[56] References Cited

U.S. PATENT DOCUMENTS

| 2,165,874 | 7/1939 | Sauls . | |
| 2,809,663 | 10/1957 | Farwick, Sr. | 137/625.41 |
| 3,800,830 | 4/1974 | Etter | 137/625.41 |
| 3,913,618 | 10/1975 | Speedie | 137/625.46 |
| 4,000,649 | 1/1977 | Hanifl | 128/762 |

FOREIGN PATENT DOCUMENTS

| 2286326 | 4/1976 | France . | |
| 559352 | 2/1975 | Switzerland . | |
| 959651 | 6/1964 | United Kingdom | 137/625.41 |

Primary Examiner—Arnold Rosenthal
Attorney, Agent, or Firm—Merriam, Marshall & Bicknell

[57] ABSTRACT

A valve for simultaneously closing the outlets of a plurality of containers in communication with the valve, and an outlet from the valve, comprising a valve housing having a plurality of inlet openings corresponding to the number of container outlets to be sealed, and at least one outlet; a sealing element adjustably positioned in the valve housing for simultaneously sealing the valve housing inlets and outlet so as to seal off liquid communication between the containers, and between the containers and the exterior; and an arm connected to the sealing element for actuation of the sealing element exterior of the valve housing.

3 Claims, 8 Drawing Figures

VALVE FOR CLOSING A PLURALITY OF CONTAINER OUTLETS SIMULTANEOUSLY

This invention relates to valves. More particularly, this invention is concerned with an adjustable valve positioned in a valve housing for simultaneously sealing or closing passages or conduits in communication with several chambers or containers. The chambers or containers may be independent of, and completely separated from, one another, and be connected by means of passages or conduits with the valve. Alternatively, the containers or chambers may be subdivisions of a larger container, e.g., a urine measuring container may be in operable communication with the valve.

To measure the hourly amount of urine drained from a catheterized patient, urine measuring instruments are used consisting, in most cases, of a rigid measuring container and a flexible urine bag. To obtain urine volume measurements as accurate as possible for use in ascertaining the patient's liquid balance, the measuring container is subdivided, by one or more partition walls, into several chambers, whereby a wider measuring scale is obtained having a correspondingly improved readability.

According to the invention there is provided a sealing member, particularly for a urine measuring container which is subdivided into several chambers, to be located between the measuring container and the urine bag, which:

1. Closes the individual containers or chambers from each other and from the primary container exterior,
2. Makes possible simultaneous emptying of all chambers into the urine bag after completion of the urine measurement,
3. Requires a small actuating force, and
4. Is inexpensive to manufacture, so it can be used once and be discarded.

The listed desirable properties are achieved by a novel valve housing having a plurality of inlet openings corresponding in number to the number of containers or chambers, to be sealed or closed by a sealing element or valve, and at least one outlet opening. The sealing element or valve, actuatable from outside the housing, prevents liquid communication between the chambers, and with the container exterior, by sealing or closing the inlet openings.

With reference to the attached drawings illustrating schematically embodiments of the invention:

Figure 1:
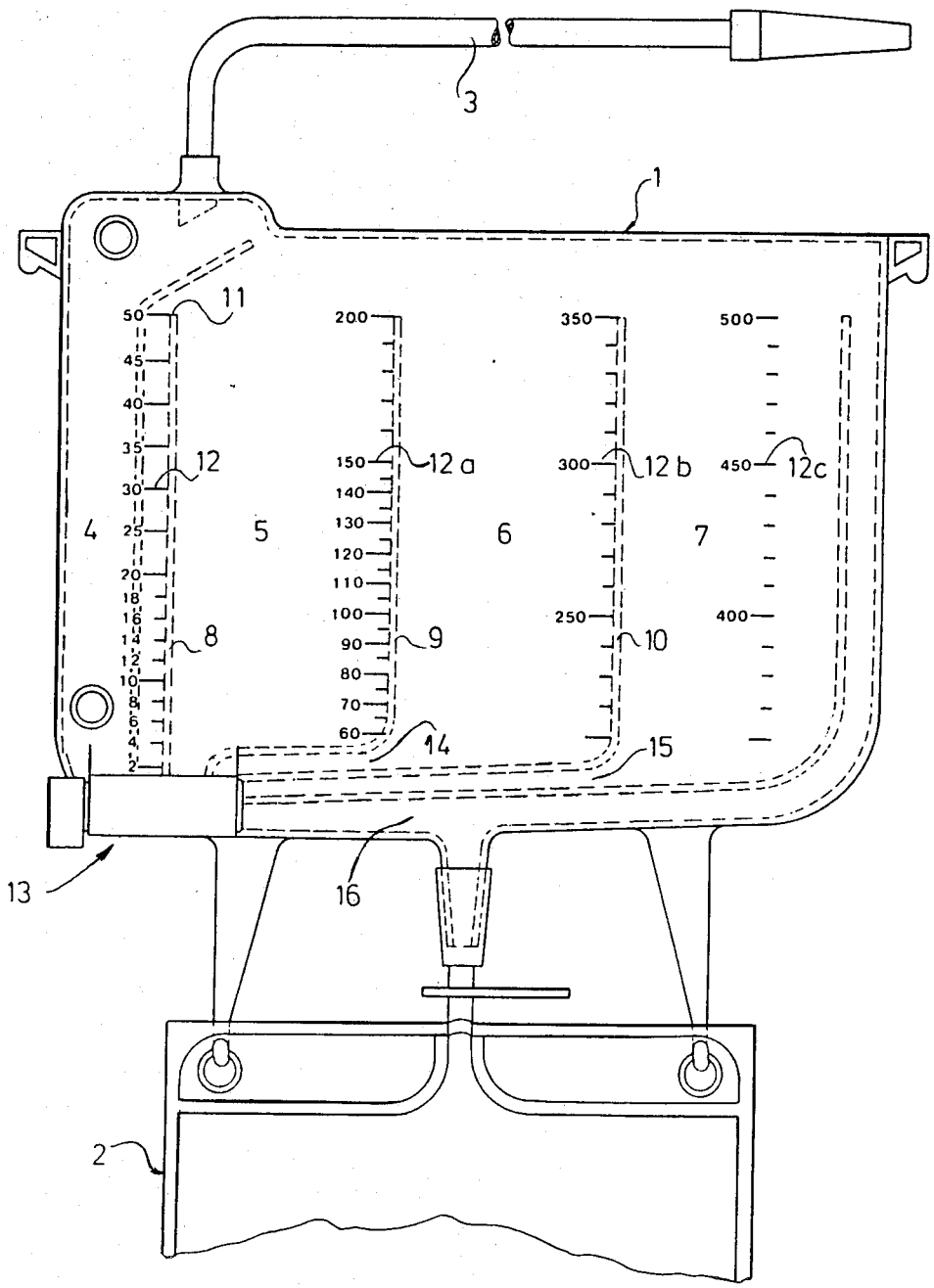
FIG. 1 shows a urine measuring instrument with a measuring container subdivided into several chambers.

With reference to FIG. 1, the urine measuring instrument consists of a measuring container 1 and a replaceable urine bag 2. The urine flows through tube 3 into the first of four chambers 4 to 7, which are formed from the container by means of partition walls 8, 9 and 10. When the first chamber 4 is full, the urine flows over the upper rim 11 of the partitioning wall 8 into the second chamber 5 and so on until all the chambers are full.

After the expiration of a predetermined period of time, the volume of collected urine is read at scale 12, 12a, 12b and 12c. Then valve 13 is opened and the urine flows from the chambers 4 and 5 directly, and from chambers 6 and 7 through passages 14 and 15, through the valve 13 to and through passage 16 into urine bag 2.

Figure 2:
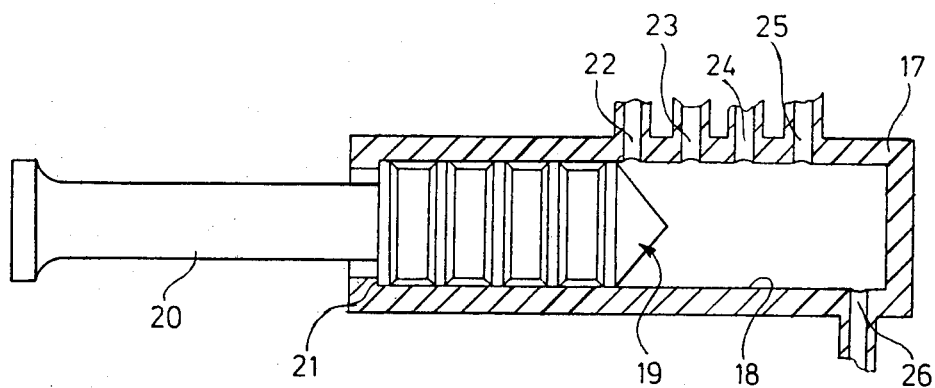
FIG. 2 shows one embodiment of valve in an open position.

The embodiment of the valve according to the invention shown in FIG. 2 consists of a valve housing 17 which, preferably, is manufactured by injecting molding of a thermoplastic synthetic material in one piece integral with the measuring container 1 for cost savings. In cylinder 18 of the housing 17 is piston 19 made of a rubber-elastic material which slides and is actuated by means of the inserted piston rod 20. Inwardly projecting corner 21 of the housing 17 prevents the piston 19 from completely slipping out of the cylinder 18. The piston is cylindrically shaped and it has several circumferential grooves 32 which are defined and bordered by continuous circumferential sealing lips or rings 27 to 31.

Inlet openings 22 to 25 of valve housing 17 are in communication, either directly or via passages 14 and 15, with the container chambers 4 to 7 shown in FIG. 1, so that the urine can flow through cylinder 18, the cylinder outlet opening 26, and the passage 16 into urine bag 2. The number of piston-circumferential grooves 32 on piston 19 corresponds to the number of inlet openings 22 to 25.

Figure 3:
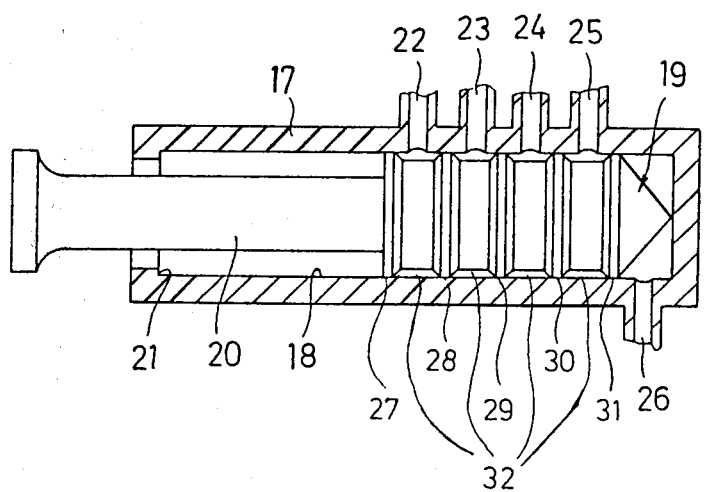
FIG. 3 shows the valve of FIG. 2 in closed position.

When the valve is in closed positon as shown in FIG. 3, the elastic sealing rings or lips 27 to 31 assume sealing functions. The sealing ring or lip 27 seals off liquid flow to the outside and the sealing ring or lip 31 seals off liquid flow to the outlet opening 26. The sealing rings or lips 28 to 30 seal off the inlet openings 22 to 25 from each other. Without such sealing the same liquid level would result in chambers 4 to 7 according to the principle of communicating tubes, and the progressive or lengthened scale 12 to 12c, which was achieved by subdividing the container 1 into individual chambers, would no longer be beneficial.

In principle, the piston 19 could have a continuous, smooth outer surface conforming to cylinder 18. Due to the grooves 32 with reduced diameter, only the sealing lips or rings 27 to 31 contact the inner surface of the cylinder 18, so that friction between the piston and cylinder, and the stick-slip effect, are reduced.

Figure 4:
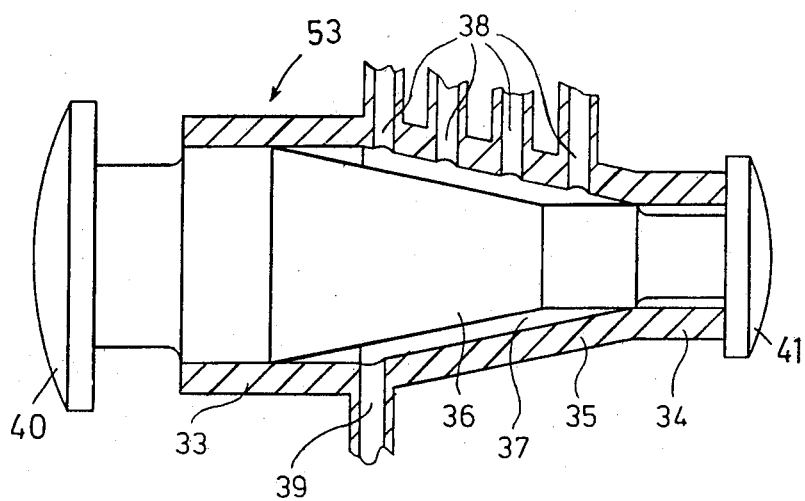
FIG. 4 shows another embodiment of the valve, with a shortened piston stroke, in open position.
Figure 5:
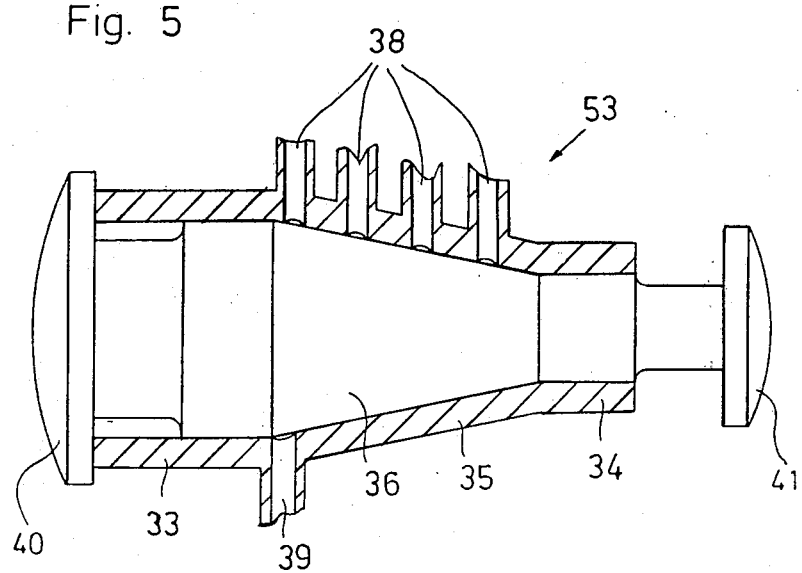
FIG. 5 shows the valve of FIG. 4 in closed position.

In a variation of the invention according to FIG. 4, the valve housing 53 consists of a cylindrical part with a larger diameter 33, a cylindrical part with a smaller diameter 34 and a conical portion 35 located between the two. A piston 36 also is subdivided into two cylindrical and one conical portions. With the valve in open position there is formed, between the housing inner wall and the piston 36, a hollow cone-shaped passage 37 through which urine can flow from the inlet openings 38 to the outlet opening 39. In the closed position (FIG. 5), the conical portions of the housing 53 and piston 36 nest together so that the housing inlet and the outlet openings are closed. The valve is actuated by two push buttons 40 and 41 which together prevent the piston 36 from slipping out of the housing 53. The advantages of this embodiment, as compared to the embodiment according to FIG. 2, are a substantially shortened piston stroke and the omission of housing corner 21 which might present problems in its manufacture. To reduce friction, the piston 36 can be equipped with several sealing lips or rings as described in discussing the embodiment of FIGS. 2 and 3.

Figure 6:
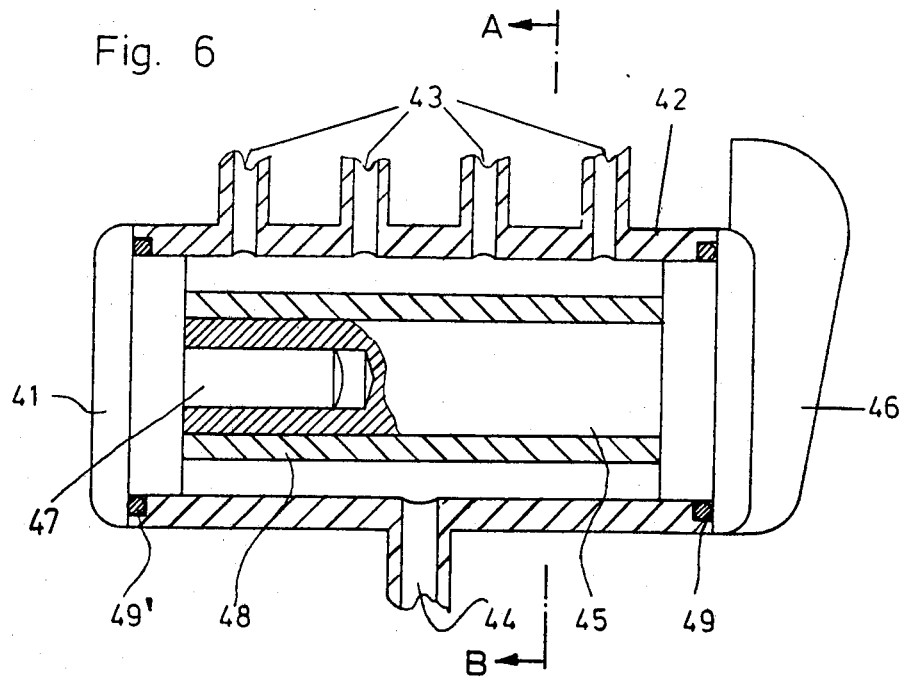
FIG. 6 shows a second embodiment of valve having an eccentric.

According to FIG. 6, this embodiment has a housing 42 with inlet and outlet openings 43 and 44, an eccentrically positioned cylindrical body 45 with a resiliently flexible tube-type soft seal 48 on its outer surface and a rotary knob 46, a pivot bearing 47 and two O-rings 49 and 49' for sealing the housing 42 against liquid leaking out. Instead of having a separate tube-type soft seal 48 on body 45, the body 45 can be made so as to be resiliently flexible at least on its outer surface and a separate seal layer made unnecessary.

Figure 7:
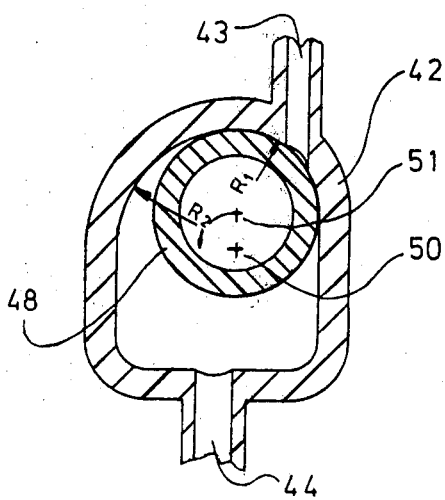
FIG. 7 is a longitudinal section through FIG. 6 along the line A–B and shows the valve in closed position.

According to FIG. 7, the eccentrically positioned body 45 rotates around point 50, which is in line with the axis of bearing 47, whereby the center 51 of the soft seal 48, in moving from the closed position to the open position, makes a counterclockwise arc of a circle in the direction of the arrow. The inner wall of the housing 42, in the area of the inlet openings 43, is provided with a radius $R_1$ around the sealing center point 51 which, for obtaining a suitable press-fit of the seal 48, is slightly smaller than the radius of the unloaded seal 48. When the eccentric is turned in the direction of the arrow to open the valve, the point of the seal 48 furthest from the center of rotation 50 describes an arc with the radius $R_2$. In this area the housing inner wall has a radius which is larger than $R_2$ to guarantee easy operating action of the valve.

Figure 8:
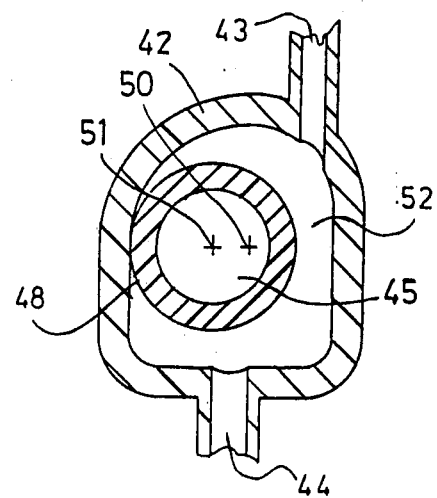
FIG. 8 shows the same section as FIG. 7, but with the valve in open position.

In the open position, according to FIG. 8, a passage 52 is formed between the seal 48 and the housing inner wall, through which the urine flows from the inlet openings 43 to the outlet opening 44.

The foregoing detailed description has been given for clearness of understanding only, and no unnecessary limitations should be understood therefrom, as modifications will be obvious to those skilled in the art.

What is claimed is:

1. A urine measuring apparatus containing a valve for simultaneously closing the outlets of a plurality of urine-receiving chambers in communication with the valve to stop flow of urine from the chambers, said valve including a housing having a plurality of aligned and spaced apart inlet openings corresponding in number to the number of chamber outlets to be sealed, and at least one outlet from the housing;

a sealing element adjustably positioned in the valve housing for simultaneously sealing all of the valve housing inlets so as to seal off liquid communication between the chambers themselves, and between the chambers and the chambers exteriors, the sealing element including a body eccentrically positioned and eccentrically pivotable in the valve housing, said valve housing being large enough to accommodate eccentric rotation of the sealing element, and means connected to the sealing element for actuation of the sealing element exterior of the valve housing.

2. A urine measuring apparatus according to claim 1 in which the sealing element is a cylindrical body.

3. A urine measuring apparatus according to claim 1 in which the sealing element is resiliently flexible at least on its outer surface.

* * * * *